(12) United States Patent
Meier et al.

(10) Patent No.: US 10,477,861 B2
(45) Date of Patent: Nov. 19, 2019

(54) EMANATION SYSTEM AND METHOD FOR USE

(71) Applicant: S. C. Johnson & Son, Inc., Racine, WI (US)

(72) Inventors: Maude Christian Meier, Racine, WI (US); Fei Gao, Chicago, IL (US); Randy C. Yuhas, Union Grove, WI (US)

(73) Assignee: S. C. Johnson & Son, Inc., Racine, WI (US)

( * ) Notice: Subject to any disclaimer, the term of this patent is extended or adjusted under 35 U.S.C. 154(b) by 0 days.

(21) Appl. No.: 15/341,373

(22) Filed: Nov. 2, 2016

(65) Prior Publication Data

US 2017/0071197 A1    Mar. 16, 2017

Related U.S. Application Data

(63) Continuation of application No. 14/309,549, filed on Jun. 19, 2014, now Pat. No. 9,522,209.
(Continued)

(51) Int. Cl.
*A61L 9/04*    (2006.01)
*A01N 25/18*    (2006.01)
(Continued)

(52) U.S. Cl.
CPC .......... *A01N 25/18* (2013.01); *A01M 1/2055* (2013.01); *A01M 29/12* (2013.01); *A01N 53/00* (2013.01);
(Continued)

(58) Field of Classification Search
CPC ... A61L 9/042; A61L 9/12; A61L 9/14; A61L 2209/134; A61L 2209/15; A01M 1/2055; A01M 29/12; A01N 65/00; A01N 25/18; A01N 53/00; B05B 11/0005; B05B 11/009
See application file for complete search history.

(56) References Cited

U.S. PATENT DOCUMENTS

| | | |
|---|---|---|
| 4,084,732 A | 4/1978 | Dearling |
| 4,283,011 A | 8/1981 | Spector |

(Continued)

FOREIGN PATENT DOCUMENTS

| | | |
|---|---|---|
| AU | 2009258191 B2 | 11/2012 |
| AU | 2013200355 A1 | 2/2013 |

(Continued)

OTHER PUBLICATIONS

International Search Report and Written Opinion of the International Searching Authority issued in PCT/US2014/044578, dated Nov. 25, 2014, 19 pages.
(Continued)

*Primary Examiner* — Davis D Hwu
(74) *Attorney, Agent, or Firm* — Quarles & Brady LLP

(57) ABSTRACT

A method of operating an emanation system is disclosed that includes the step of providing a dispensing device containing an air treatment material and a substrate. The method further includes the steps of aligning a nozzle of the dispensing device with the substrate and actuating the dispensing device to spray an amount of the air treatment material onto at least a portion of the substrate.

20 Claims, 7 Drawing Sheets

Related U.S. Application Data

(60) Provisional application No. 61/840,561, filed on Jun. 28, 2013, provisional application No. 61/944,307, filed on Feb. 25, 2014.

(51) Int. Cl.
    *A61L 9/12* (2006.01)
    *A01M 29/12* (2011.01)
    *A01M 1/20* (2006.01)
    *A01N 53/00* (2006.01)
    *A61L 9/14* (2006.01)
    *B05B 11/00* (2006.01)

(52) U.S. Cl.
    CPC .............. *A61L 9/042* (2013.01); *A61L 9/12* (2013.01); *A61L 9/14* (2013.01); *B05B 11/0097* (2013.01); *A61L 2209/134* (2013.01); *A61L 2209/15* (2013.01)

(56) References Cited

U.S. PATENT DOCUMENTS

| | | | |
|---|---|---|---|
| 4,346,059 A | 8/1982 | Spector | |
| 4,419,396 A | 12/1983 | Sugimoto | |
| 4,696,844 A | 9/1987 | Spector | |
| 4,797,310 A * | 1/1989 | Barby .................... | A47L 13/17 428/316.6 |
| 4,961,930 A | 10/1990 | Perdelwitz, Jr. et al. | |
| 5,139,864 A | 8/1992 | Lindauer | |
| 5,738,862 A | 4/1998 | Abraham | |
| 5,792,465 A | 8/1998 | Hagarty | |
| D435,100 S | 12/2000 | Pesu et al. | |
| 6,551,560 B1 | 4/2003 | Flahinski | |
| 8,048,517 B2 | 11/2011 | Kimball et al. | |
| 8,191,796 B2 | 6/2012 | Lammert et al. | |
| 9,149,416 B1 | 10/2015 | Xie | |
| 2004/0223998 A1* | 11/2004 | Iyer ....................... | A01N 65/00 424/405 |
| 2005/0196571 A1 | 9/2005 | Penny, III et al. | |
| 2009/0090466 A1 | 4/2009 | Huppert et al. | |
| 2010/0056422 A1 | 3/2010 | Lammert et al. | |
| 2010/0096414 A1* | 4/2010 | Dennis ................ | B05B 11/0005 222/383.1 |
| 2011/0097506 A1 | 4/2011 | Shah et al. | |
| 2013/0255728 A1* | 10/2013 | Noh ....................... | B05B 13/02 134/26 |

FOREIGN PATENT DOCUMENTS

| | | |
|---|---|---|
| CN | 1341357 A | 3/2002 |
| CN | 1669428 A | 9/2005 |
| CN | 101176464 A | 5/2008 |
| CN | 102028371 A | 4/2011 |
| CN | 202285973 U | 7/2012 |
| CN | 102745635 A | 10/2012 |
| DE | 20215305 U1 | 12/2002 |
| DE | 10 2007 062 315 A1 | 6/2009 |
| EP | 0907317 B1 | 1/2003 |
| GB | 2 382 027 A | 5/2003 |
| IN | 22/2009 | 5/2009 |
| WO | 2008/012507 A1 | 1/2008 |
| WO | 2013/14456 A1 | 10/2013 |

OTHER PUBLICATIONS

PCT/US2014/044578 International Search Report and Written Opinion dated Nov. 25, 2014.
Annex to Form PCT/ISA/2016 Communication Relating to the Results of the Partial International Search, issued in PCT Application No. PCT/US014/044578, dated Oct. 1, 2014, 2 pages.
First Office Action (including English translation) issued in corresponding Chinese Patent Application No. 201480040562.7, dated May 4, 2017, 19 pages.
Second Office Action (including English translation) issued in corresponding Chinese Patent Application No. 201480040562.7, dated Jan. 3, 2018, 16 pages.

\* cited by examiner

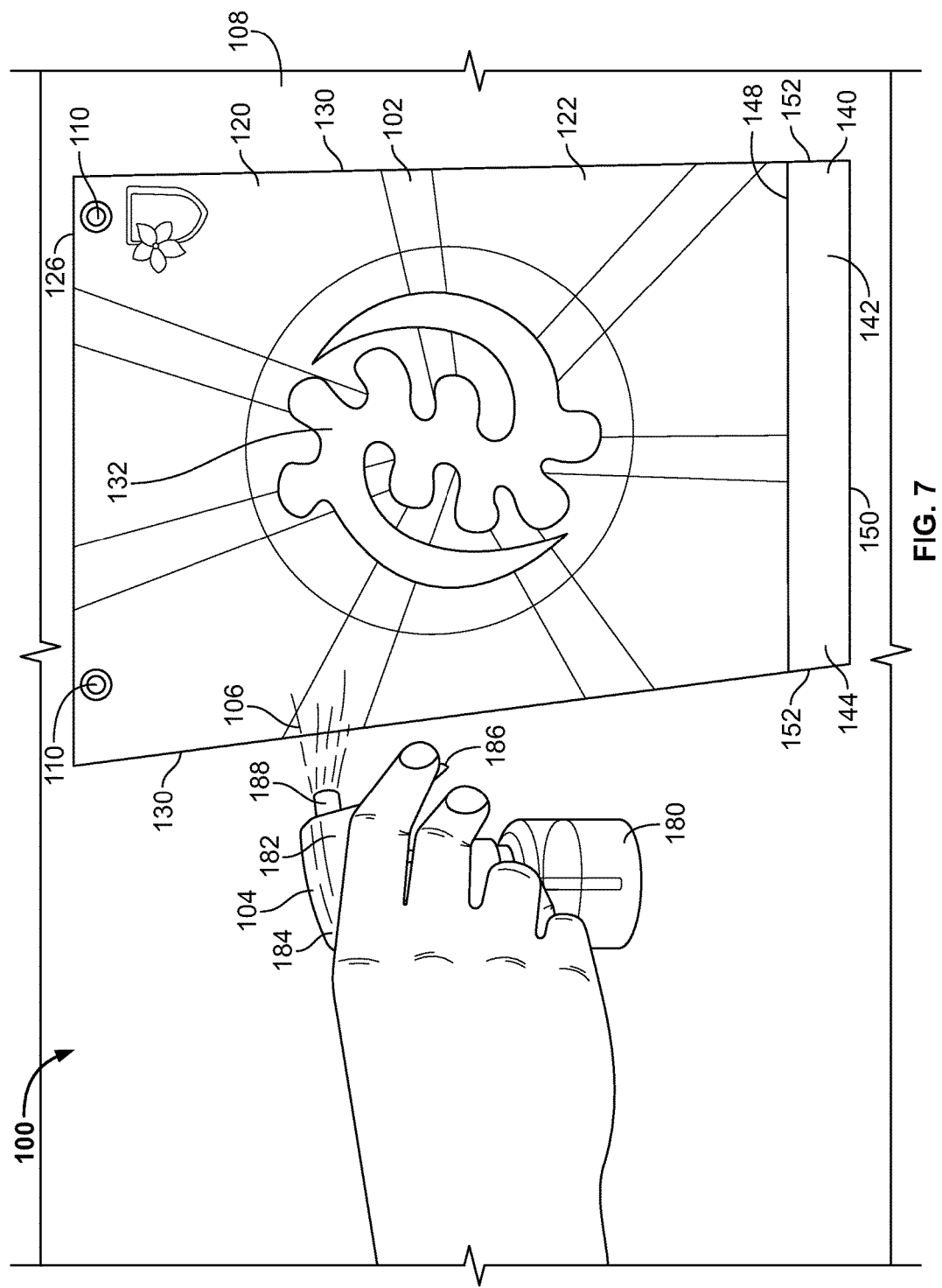

EMANATION SYSTEM AND METHOD FOR USE

CROSS REFERENCE TO RELATED APPLICATIONS

This application is a divisional of U.S. patent application Ser. No. 14/309,549, filed on Jun. 19, 2014, which claims priority to U.S. Provisional Application Ser. No. 61/840,561, filed Jun. 28, 2013, and to U.S. Provisional Application Ser. No. 61/944,307, filed Feb. 25, 2014.

REFERENCE REGARDING FEDERALLY SPONSORED RESEARCH OR DEVELOPMENT

Not applicable.

SEQUENCE LISTING

Not applicable.

BACKGROUND OF THE DISCLOSURE

1. Field of the Disclosure

The present disclosure relates to emanation systems with one or more substrates attached to a surface, and in particular, to a substrate with a visual guide disposed thereon and having one or more active release profiles.

2. Description of the Background of the Disclosure

Various emanation systems are known in the prior art that generally include a reservoir that holds a volatile material and optionally includes a housing or support structure to retain the reservoir. The prior art emanation systems typically either allow passive diffusion of the volatile material to occur without the aid of a dispensing mechanism or enhance and/or facilitate the release of the volatile material using a dispensing mechanism. Typical dispensing mechanisms used in emanation systems include a heating device and/or a fan that either heats and/or supplies air, respectively.

Many passive emanation systems of the prior art utilize a solid or semi-solid block of material or a volatile material laden gel disposed within a housing. In particular, one prior art emanation system includes a container having a candle therein. When lit, the candle emits a volatile material. Another prior art emanation system uses a conical gel surface impregnated with a volatile material. The conical gel surface is disposed within a housing having an adjustable cap. The cap may be adjusted upwardly or downwardly to expose the surface area of the conical gel surface to varying degrees. In a different prior art emanation system, a reservoir having a semi-permeable film disposed thereon is used and has a volatile material disposed within the reservoir. The volatile material diffuses out of the reservoir through the semi-permeable membrane. Another prior art emanation system includes a substantially flat substrate having a volatile material thereon. The volatile material is slowly released into the surrounding atmosphere.

One drawback of some of the aforementioned prior art emanation systems is that the substrate may be wetted with a volatile material that is released over a shortened time period. The release profile of the volatile material is generally constant in that the release rate of the volatile slowly decreases until the volatile is evaporated. In these systems, the emanation system only provides efficacy for a short period of time after application of the volatile to the substrate.

Further, some prior art emanation systems are designed to emit an insecticide. Historically, the smell of the insecticide has been unpleasant, which sometimes discourages use of the emanation system. Some attempts have been made to mask the unpleasant odor associated with the use of insecticides through the incorporation of citronella oil into the emanation system.

Further, in some instances, it is undesirable to keep air treatment materials within the home. Therefore, it is desirable to have an emanation system in the home that can be refilled by a third party such that the air treatment materials do not need to be kept in the home. In some instances, it may also be desirable to have the third party re-apply the air treatment materials to the emanation system so that individuals do not have to touch the material-laden surface of the substrate after use.

Therefore, it would be desirable to have an inexpensive passive emanation system in the form of a wettable substrate that allows a user to apply an air treatment material thereto. It is further desirable to provide a system that allows the air treatment material to emanate at a high rate after the initial application of the air treatment material to the substrate, and further allows for continued efficacy by having a secondary substrate that releases the air treatment material at a slower rate than that of the substrate. Finally, it would be desirable to have a fragrance incorporated into the air treatment material, which acts to incentivize the user to use the emanation system, and also acts as a use-up cue that allows the user to determine when the air treatment material is no longer effective.

SUMMARY OF THE INVENTION

According to a first aspect, an emanation system includes a substrate, a secondary substrate, and an air treatment material. The secondary substrate is adapted to be wetted with runoff from the air treatment material applied to the substrate. When applied, the air treatment material emanates from the substrate at a first release rate and from the secondary substrate at a second release rate.

The following attributes may be combined individually or in any combination with the first aspect to form different embodiments of the first aspect: the substrate may include a substantially rectangular body and the secondary substrate may be disposed adjacent a lower edge of the body; the secondary substrate may be in communication with the substrate such that a rear surface of the secondary substrate is substantially flush with a front surface of the substrate; the substrate may include a polymer and the secondary substrate may include a cellulosic material; the substrate and the secondary substrate may define a substantially smooth surface; and the substrate may include a visual guide.

According to a second aspect, an air treatment material includes a fragrance having a first efficacy time period and an active ingredient having a second efficacy time period. The air treatment material is provided as a microemulsion, and the first and the second efficacy time periods are substantially the same.

The following attributes may be combined individually or in any combination with the second aspect to form different embodiments of the second aspect: the air treatment material may be applied to a polymer substrate and the active ingredient may be released therefrom at a rate of at least about 0.2 mg/hr; the fragrance may act as a use-up indicator to provide an olfactory cue that the second efficacy time period has ended; the active ingredient may be a pyrethroid; the air treatment material may further include a surfactant blend; the air treatment material may include about 4% fragrance and about 0.4% active ingredient; and the air treatment material may include about 90% of deionized water, about 3 to about 6% of the surfactant blend, about 2 to about 6% of the fragrance, and about 0.2 to about 1% of the active ingredient.

According to a third aspect, a method of operating an emanation system includes the steps of providing a dispensing device containing an air treatment material and a substrate, aligning a nozzle of the dispensing device with the substrate, and actuating the dispensing device to spray an amount of the air treatment material onto at least a portion of the substrate.

The following attributes may be combined individually or in any combination with the third aspect to form different embodiments of the third aspect: a secondary substrate may be designed to catch an amount of run off from the amount of air treatment material sprayed onto the substrate; the air treatment material may emanate from the substrate at a first release rate, and may emanate from the secondary substrate at a second release rate; the method of the third aspect may further include the step of filling the dispensing device; the nozzle may be aligned with a visual guide on the substrate; the amount of air treatment material sprayed may be about 3 grams; and the amount of the air treatment material sprayed onto the substrate may provide mosquito repellency and a pleasant fragrance to the room for a time period of about three days.

BRIEF DESCRIPTION OF THE DRAWINGS

FIG. 7 is a perspective view of the emanation system of FIG. 1 in use.

DETAILED DESCRIPTION OF THE INVENTION

Figure 1:
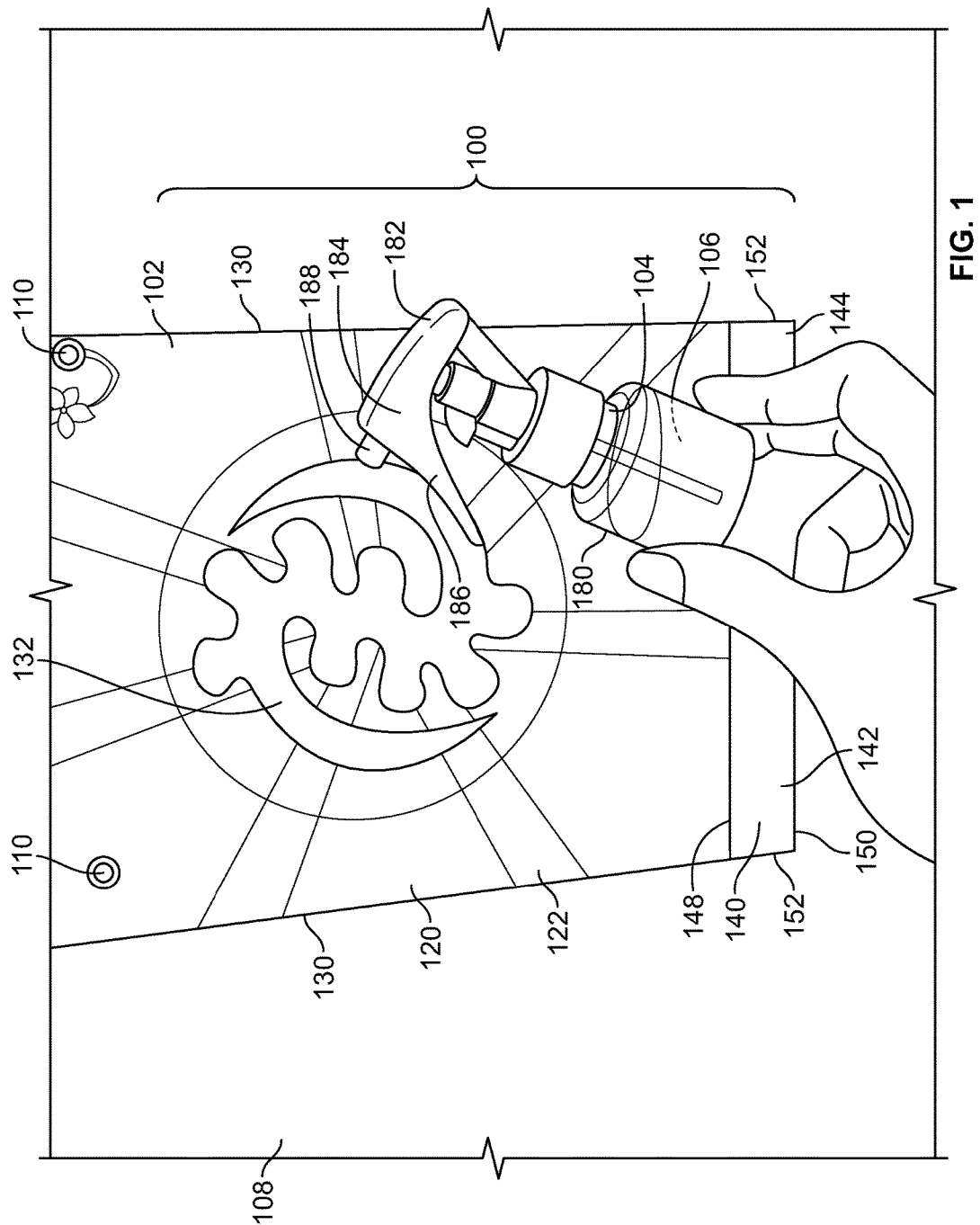
FIG. 1 is a perspective view of a first embodiment of an emanation system having a substrate and a dispensing device associated therewith.

As generally depicted in FIGS. 1-7, an emanation system 100 generally includes a substrate 102 and a dispensing device 104 designed to coat the substrate 102 with an air treatment material 106. The emanation system 100 may be used in an enclosed area, such as an office, a living room, a bedroom, a kitchen, a screened in porch, a basement, or other suitable location. Prior to use, the substrate 102 may be attached to a surface 108 via an attachment mechanism 110. During use, the dispensing device 104 is positioned adjacent the substrate 102, and the air treatment material 106 is dispensed onto the substrate 102. The emanation system 100 is adapted to passively dispense the air treatment material 106 from the substrate 102 when air flows around the substrate.

The substrate 102 may have a rectangular body 120 with a front surface 122, a rear surface 124, upper 126 and lower 128 edges, and opposing side edges 130. In one embodiment, the substrate 102 has a flat, smooth appearance. The substrate 102 may have various textures and/or surface patterns, such as a rough surface, a smooth surface, a channeled surface, and combinations thereof that may increase surface area and/or the rate of emanation of the air treatment material 106. Moreover, the substrate 102 may be any shape such as square, triangular, circular, oval, and other shapes.

Figure 2:
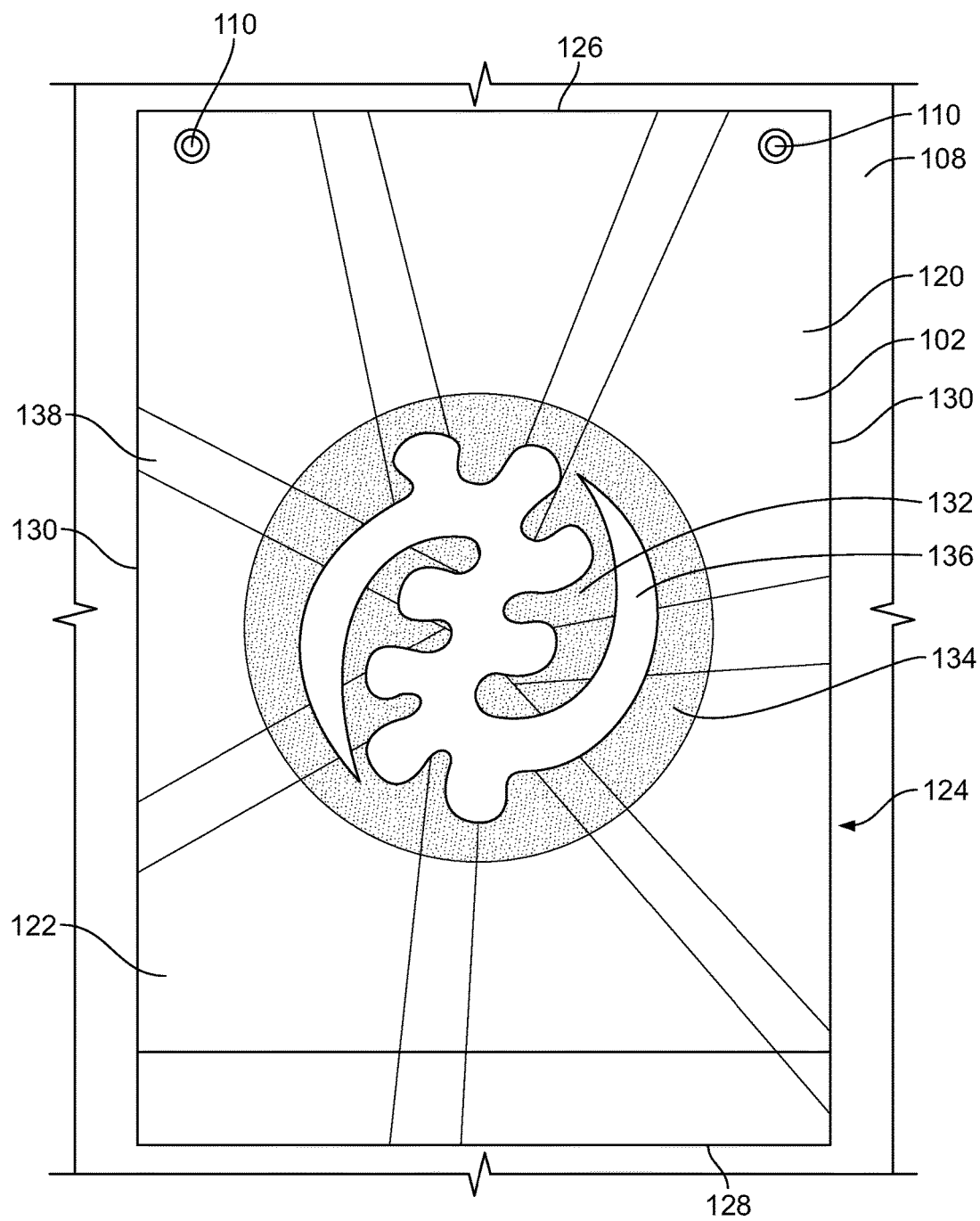
FIG. 2 is a perspective view of a substrate similar to that of FIG. 1, wherein the substrate is attached to a surface via an attachment mechanism.
Figures 3A, 3B:
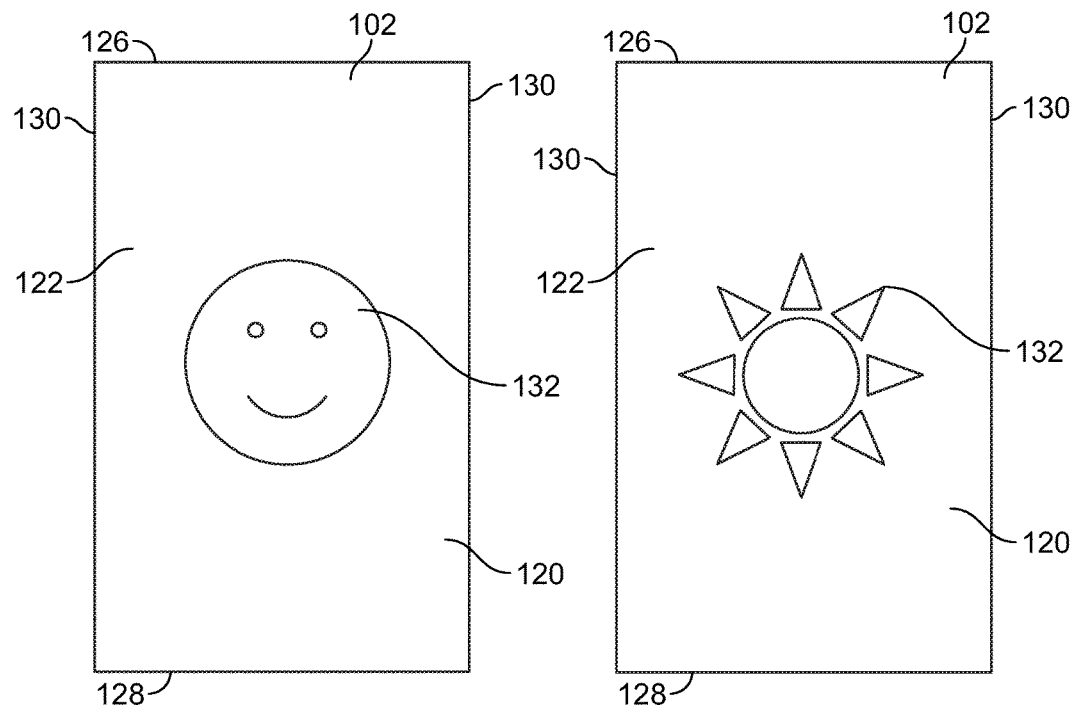
FIG. 3A is a schematic of one embodiment of a substrate with a visual guide.
FIG. 3B is a schematic of another embodiment of a substrate with a visual guide.
Figures 3C, 3D:
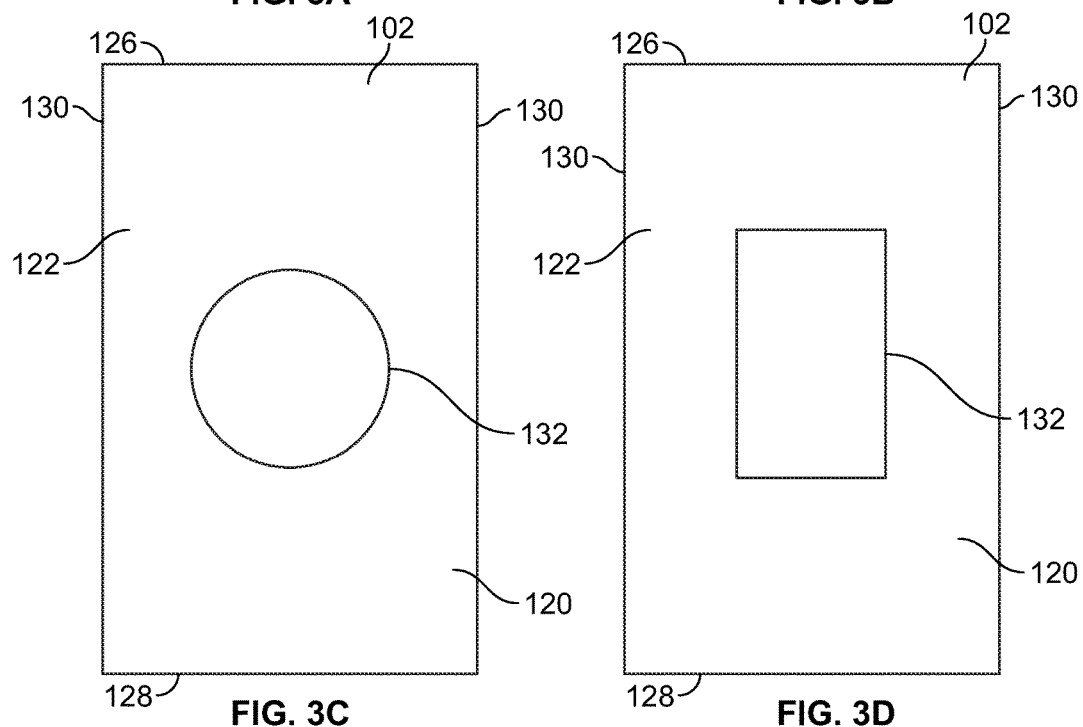
FIG. 3C is a schematic of a different embodiment of a substrate with a visual guide.
FIG. 3D is a schematic of another embodiment of a substrate with a visual guide.
Figure 3E:
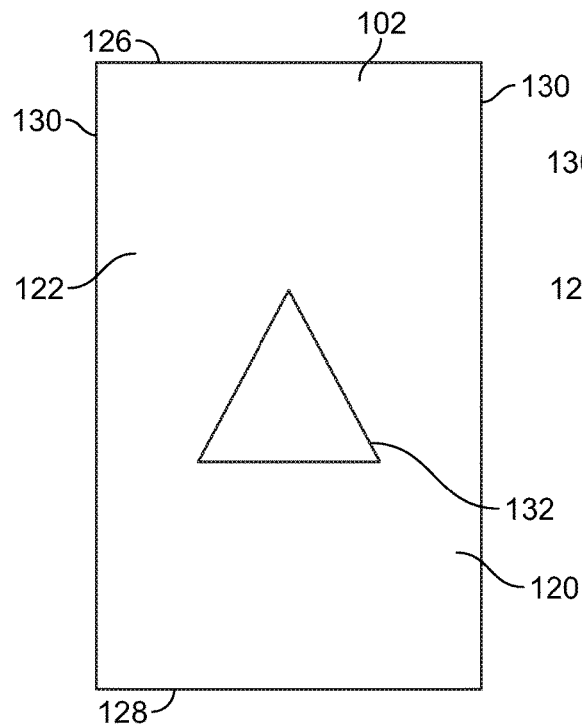
FIG. 3E is a schematic of one embodiment of a substrate with a visual guide.
Figure 3F:
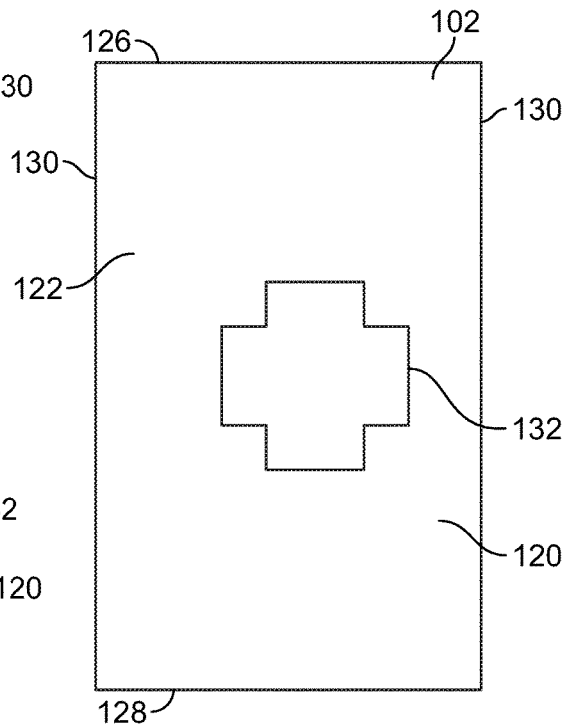
FIG. 3F is a schematic of another embodiment of a substrate with a visual guide.
Figure 3G:
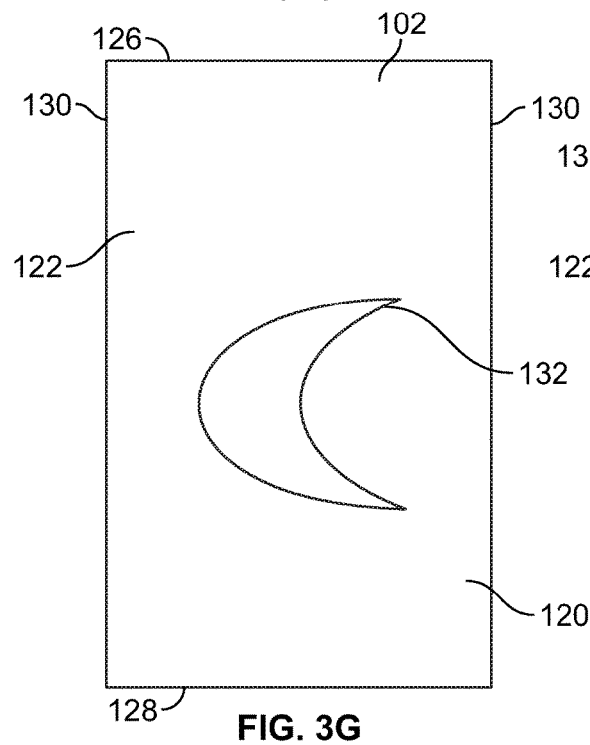
FIG. 3G is a schematic of a different embodiment of a substrate with a visual guide.
Figure 3H:
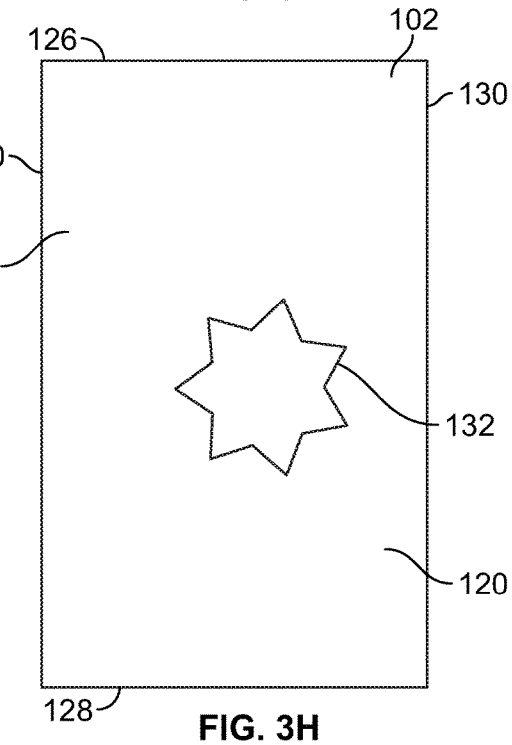
FIG. 3H is a schematic of another embodiment of a substrate with a visual guide.

As seen more clearly in FIGS. 2-3H, the substrate 102 may further include a spray pattern or visual guide 132 disposed thereon. The visual guide 132 may be positioned on either the front 122 or rear surface 124 of the substrate 102, and may be visible through the substrate. In one instance, the visual guide 132 includes a dark circular boundary 134 with a contrasting pattern 136 therein, as compared to the color of the substrate 102. A secondary pattern 138 is optionally provided in conjunction with the visual guide 132 and may provide an aesthetic quality to the substrate 102.

The visual guide 132 may act as a target or non-verbal cue for an individual coating the substrate 102 with the air treatment material 106, as described in more detail hereinbelow. The visual guide 132 may be only a region of visual contrast from the surrounding substrate 102, though any pattern or visual device may be used. For example, numerous representative examples of exemplary visual guides 132 are depicted in FIGS. 3A-3H.

In some embodiments, the visual guide 132 directs an individual coating the substrate 102 where to spray the air treatment material 106 and provides a secondary meaning. For example, the visual guide 132 depicted in FIG. 3A may indicate that the substrate 102 and associated air treatment material 106 are non-toxic and/or environmentally friendly. In other embodiments seen in FIGS. 3B, 3G, or 3H, the visual guides 132 may depict images suggesting a time of day (e.g., day or night) to indicate when the substrate 102 and associated air treatment material 106 should be used.

In other embodiments, the pattern or appearance of the visual guide 132 may be correlated either with a dispensing pattern of the dispensing device 104 or may otherwise indicate a pairing with the dispensing device. With respect to the first concept, the dispensing device 104 may dispense the air treatment material 106 in the same shape as the visual guide 132 disposed on the substrate 102, such as a circular pattern (FIG. 3C), a rectangular pattern (FIG. 3D), or a triangular pattern (FIG. 3E). Regarding the second concept, the pattern of the visual guide 132 may be indicative of which air treatment material 106 should be used for the particular substrate 102. For example, a particular substrate 102 may have a characteristic that favors one type of air treatment material 106 compared to another, such as an ideal emanation rate for the air treatment material in question due to the material from which the particular substrate is made.

In other words, the visual guide 132 serves to instruct the user which air treatment material 106 should be used with the substrate 102, and the user matches the pattern of the visual guide to that disposed (not shown) on the dispensing device 104.

In further embodiments, contact between the air treatment material 106 and the substrate 102 changes the appearance of the visual guide 132. For example, in one instance, the visual guide 132 disappears or fades or changes color after contact with the air treatment material 106. In a different embodiment, the visual guide 132 becomes visible only after contact with the air treatment material 106 and fades over time. In this embodiment, the visual guide 132 may fade as the efficacy of the air treatment material lessens to serve as a visual use up cue.

As seen in FIGS. 1, 4, 5, and 7, the substrate 102 may further include a secondary substrate 140 associated therewith. The secondary substrate 140 may be provided in the form of a rectangular sheet 142 having a front surface 144 and an opposing rear surface 146. The sheet 142 has an upper edge 148, a lower edge 150, and opposing side edges 152. The secondary substrate 140 is attached to, or is otherwise in communication with the substrate 102. In particular, the secondary substrate 140 may be positioned such that the rear surface 146 of the secondary substrate 140 is flush with the front surface 122 of the substrate 102. Further, the lower edge 128 and side edges 130 of the substrate 102 may be aligned with the corresponding lower edge 150 and side edges 152 of the secondary substrate 140. In other embodiments, the secondary substrate 140 may be larger, smaller, and/or wrap around one or more edges 126, 128, 130 of the substrate 102.

The secondary substrate 140 may be attached to the substrate 102 by an adhesive, a staple, a hook and loop fastener, combinations thereof, and other mechanisms. In one embodiment, the secondary substrate 140 is designed to be adjacent the front surface 122 of the substrate 102 such that there are no gaps between the substrate 102 and the secondary substrate 140. In another embodiment, the secondary substrate 140 is disposed on the substrate 102 to serve as the visual guide 132.

Figure 4:
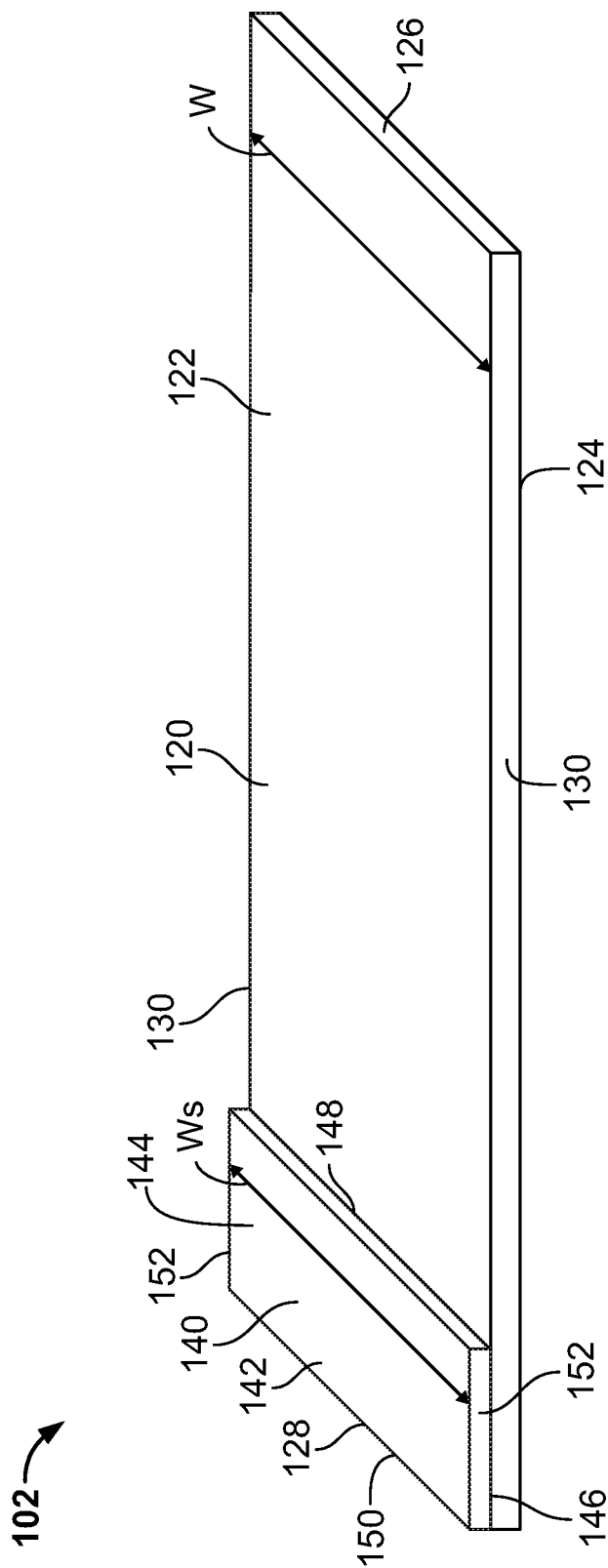
FIG. 4 is a front, right, top isometric view of a substrate similar to that of FIG. 1.
Figure 5:
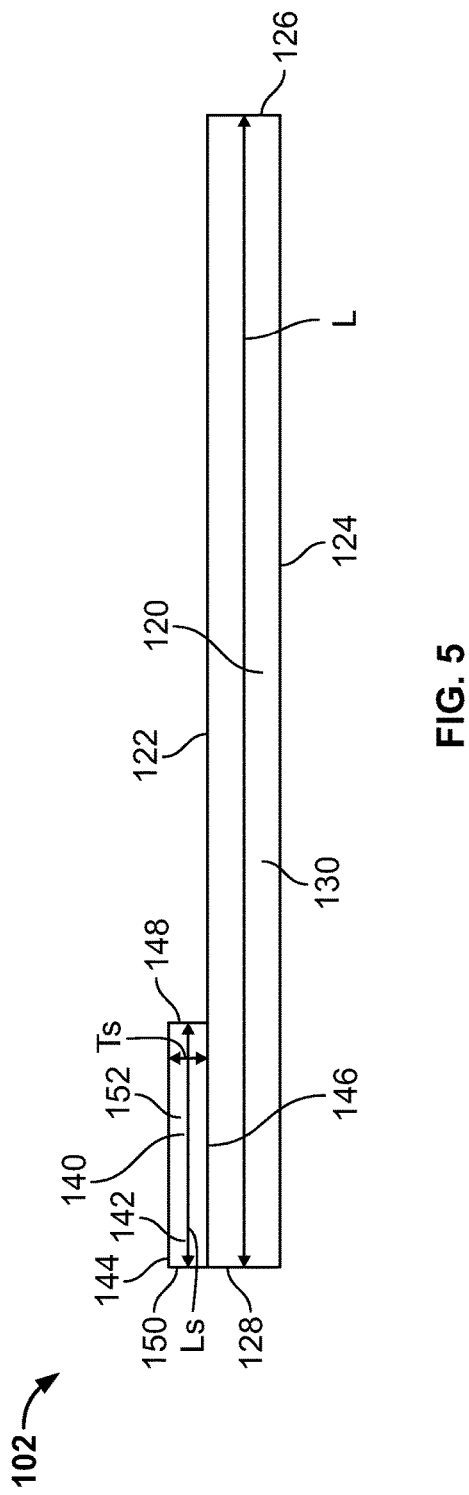
FIG. 5 is side elevational view of the substrate of FIG. 4.

Referring to FIGS. 4 and 5, the substrate 102 may have a length dimension L of between about 10 mm to about 800 mm. In some embodiments, the length dimension L of the substrate 102 is between about 100 mm to about 500 mm. In one specific embodiment, the length dimension L of the substrate 102 is about 300 mm. The substrate 102 further may have a width dimension W of between about 10 mm to about 600 mm. In some embodiments, the width dimension W of the substrate 102 is between about 100 mm to about 400 mm. In one specific embodiment, the width dimension W of the substrate 102 is about 210 mm.

As depicted in FIG. 5, the secondary substrate 140 may have a thickness dimension $T_s$ of between about 0.1 mm to about 2 mm. In some embodiments, the thickness dimension $T_s$ of the secondary substrate 140 is between about 0.3 mm to about 1 mm. In one specific embodiment, the thickness dimension $T_S$ of the secondary substrate 140 is about 0.6 mm. In another embodiment, the thickness dimension $T_S$ of the secondary substrate 140 is at least about 0.4 mm. The secondary substrate 140 further may have a length dimension $L_S$ of between about 1 mm to about 100 mm. In some embodiments, the length dimension $L_S$ of the secondary substrate 140 is between about 5 mm to about 100 mm. In one specific embodiment, the length dimension $L_S$ of the secondary substrate 140 is about 25 mm. In another embodiment, the length dimension $L_S$ of the secondary substrate 140 is at least about 20 mm.

The secondary substrate 140 further may have a width dimension $W_S$ (see FIG. 4) of between about 10 mm to about 600 mm. In some embodiments, the width dimension $W_S$ of the secondary substrate 140 is between about 100 mm to about 400 mm. In one specific embodiment, the width dimension $W_S$ of the secondary substrate 140 is about 210 mm. In one embodiment, the width dimension W of the substrate 102 is substantially the same as the width dimension $W_S$ of the secondary substrate 140. In one embodiment, the ratio of the length dimension L of the substrate 102 to the length dimension $L_S$ of the secondary substrate 140 is about 14 to about 1. In another embodiment, the ratio of the length dimension L of the substrate 102 to the length dimension $L_S$ of the secondary substrate 140 is about 10 to about 1. In a further embodiment, the ratio of the length dimension L of the substrate 102 to the length dimension $L_S$ of the secondary substrate 140 is about 8 to about 1.

Figure 6:
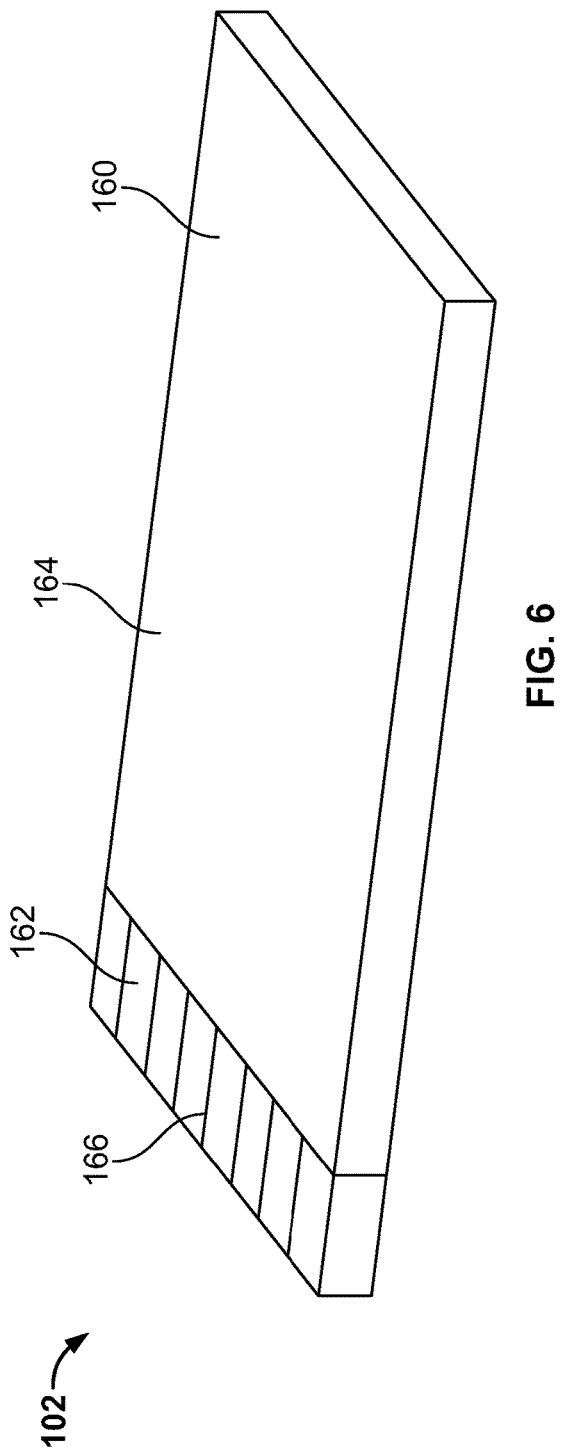
FIG. 6 is a front, right, top isometric view of a different embodiment of a substrate.

As seen in FIG. 6, the substrate 102 may include a first emanation surface 160 and a second emanation surface 162. In this embodiment, the first emanation surface 160 and the second emanation surface 162 are integral, or otherwise in fixed communication with each other to form the substrate 102. The first and second emanation surfaces 160, 162 may be integral, in that, the substrate 102 is provided as a single sheet with a portion of the sheet having a different volatile material release profile from other portions of the sheet. In this embodiment, the substrate 102 includes a substantially uninterrupted front surface 164. Although the second emanation surface 162 is depicted as an elongate rectangular structure, the second emanation surface 162 may include other shapes and/or sizes and/or may be oriented or positioned in other portions of the substrate 102.

A demarcation between the substrate 102 and the secondary substrate 140, or the first and second emanation surfaces 160, 162, may not be readily apparent unless another mechanism (e.g., visual cue) is used to alert the user. For example, the second emanation surface 162 may be imparted with a pattern 166 or design, while the first emanation surface 160 may not include the pattern or design. In other embodiments, the first and second emanation surfaces 160, 162 may be contrasted using patterns, colors, and/or other visual markers. In a further embodiment, the first and second emanation surfaces 160, 162 are not visually distinct with respect to each other. Likewise, the substrate 102 and/or secondary substrate 140 may be provided with one or more visual cues distinguishing one from the other.

The substrate 102 may be chosen based on the rate of release from the substrate of a composition impregnated therein. For example, the substrate 102 may be chosen to have a release rate such that an effective amount of a pest control agent, such as an insecticide or insect repellant, is released for a specific length of time, such as for about 1 day, or about 2, or about 3, or about 7, or about 14 days. Further, the substrate 102 may also be chosen based on its ability to maximally release a composition held therein, such that at the end of life, a minimal amount of composition is still contained therein.

The materials and properties used for the substrate 102 and/or the secondary substrate 140 impact the volatile material release rates of each substrate. Therefore, the substrate 102 may include a first volatile material release profile, and the secondary substrate 140 may include a second, different, volatile material release profile. In one embodiment, an active contained within the air treatment material 106 may be designed to be released from the substrate 102 at a rate of about 0.1 mg/hr to about 1 mg/hr. In other embodiments, the active may be released from the substrate 102 at a rate of about 0.1 mg/hr to about 0.3 mg/hr. In a further embodiment, the active may be released from the substrate 102 at a rate of about 0.25 mg/hr. In another embodiment, the active may be released from the substrate 102 at a rate of at least about 0.2 mg/hr. Contemplated effective release rates of the active from the secondary substrate 140 may be from about 0.01 mg/hr to about 1 mg/hr. In other embodiments, the active may be released from the secondary substrate 140 at a rate of about 0.05 mg/hr to about 0.1 mg/hr, or from about 0.05 to about 0.2 mg/hr, or from about 0.1 to about 0.3 mg/hr. In another embodiment, the active may be released from the secondary substrate 140 at a rate of less than about 0.1 mg/hr. In one embodiment, the active may be released from the secondary substrate 140 at a slower rate than the release rate of the active from the substrate 102. It should be noted that the substrate 102 may be defined by the second volatile material release profile, and the secondary substrate 140 may be defined by the first volatile material release profile.

Any suitable materials may be used for the substrate 102 and secondary substrate 104. For example, the substrate 102 may be made of paper, cardboard, paperboard, plastic, and the like, or other materials consistent with the properties described herein. In one embodiment, the substrate 102 may include a natural or synthetic plastic material. For example, in one embodiment, the substrate 102 includes a polymer such as polypropylene, polyethylene, and/or polyethylene terephthalate. In one particular embodiment, the substrate 102 is a polyethylene terephthalate film.

The secondary substrate 140 may include a material that is rigid enough to minimize any gaps between the secondary substrate and the substrate 102, while at the same time, porous enough to absorb a quantity of air treatment material 106. For example, the secondary substrate 140 may be paper, cardboard, paperboard, foam, or the like. The secondary substrate 140 may include cellulosic materials including crepe paper, printer paper, A4 paper, and materials disclosed in WO 2005/046332. Additionally, the substrate 102 and/or the secondary substrate 140 may include combinations of manufactured, natural, and recycled or reclaimed materials. In one specific embodiment, the substrate 102 includes a polymer and the secondary substrate 140 includes cardboard.

Further, one or more portions of or the entirety of the substrate 102 may be transparent. In addition, one or more portions of or the entirety of the substrate 102 and/or the secondary substrate 140 may be translucent and/or opaque. Further, any combination of transparency, translucency, or opacity may be chosen for the substrate 102 and the secondary substrate 140. For example, in one embodiment, the substrate 102 is translucent, and the secondary substrate 140 is opaque. In another embodiment, both the substrate 102 and the secondary substrate 140 are transparent. In a further embodiment, the substrate 102 is opaque, and the secondary substrate 140 is translucent.

The air treatment material 106 may be a fragrance or insecticide disposed within a carrier liquid, a solvent, a deodorizing liquid, and the like. The air treatment material 106 may also include other actives, such as sanitizers, air fresheners, odor eliminators, mold or mildew inhibitors, insect repellents, and the like, or actives that have aromatherapeutic properties. The air treatment material 106 alternatively includes any volatile material known to those skilled in the art.

The air treatment material 106 may be provided in any dispensable form. In one embodiment, the air treatment material 106 is provided as an emulsion. For example, the air treatment material 106 may be provided as a microemulsion. In one embodiment, the air treatment material 106 may include water, one or more surfactants, an active ingredient, and a fragrance.

In one embodiment, the air treatment material 106 may include between about 80% to about 98% deionized water, or about 85% to about 94% deionized water, or about 90% deionized water, or an amount of deionized water of at least about 80% of the total of the air treatment material.

The air treatment material 106 may further include a surfactant and/or a surfactant blend provided in an amount between about 0.1% to about 8%. In one embodiment, the surfactant blend is provided in an amount between about 3% to about 6%. In a different embodiment, the surfactant blend is present in an amount of at least about 4%. In one specific embodiment, a first surfactant is provided in an amount between about 0.1% to about 0.5%, a second surfactant is provided in an amount between about 1.75% to about 2.5%, and a third surfactant is provided in an amount between about 1.75% to about 2.5%. Suitable surfactants include, for example, nonionic, anionic, zwitterionic, and/or cationic surfactants. For example, the first surfactant may be provided by Stepan, Co. under the trade name and number Stepanquat® 1010, and the second surfactant may be provided by Dow Chemical, Co. under the name and number Tergitol™ 15-S-7. The third surfactant may be an ethoxylated castor oil provided by Evonik Industries and sold under the name and number Tagat® CH 60.

The air treatment material 106 may also include at least one fragrance. The fragrance may be present in an amount of between about 0.5% to about 10%, or about 2% to about 6%, or in an amount at least about 4%. Any fragrance may be used herein including, for example, a floral scent, a fresh scent, a lavender scent, a eucalyptus scent, a pine scent, a spice scent, and combinations thereof.

An active ingredient may be present in the air treatment material 106 in an amount of between about 0.1% to about 2%, or about 0.2% to about 1%, or in an amount of about 0.4%, or at least about 0.3%. Candidate actives include esbiothrin, tefluthrin, prallethrin, transfluthrin, VAPORTHRIN®, metofluthrin, dimefluthrin, D-tefluthrin, and/or other volatile pyrethroids (with high vapor pressure). An active release rate of at least 0.05 milligrams per hour (mg/hr) or higher is preferred.

In one specific embodiment, the air treatment material 106 includes about 90.7% (2.7 g) of deionized water, about 0.4% (0.01 g) of the first surfactant, about 2.25% (0.068 g) of the second surfactant, about 2.25% (0.068 g) of the third surfactant, about 4% (0.12 g) of the fragrance, and about 0.4% (0.012 g) of the active ingredient.

It is contemplated that fragrances may be used as "use up" cues or indicators, such that when a user can no longer smell the fragrance, the strength of the active ingredient is no longer effective for its intended purpose, and the substrate 102 must be "recharged" with another dose of the air treatment material 106. In one embodiment, the amount of fragrance included in the air treatment material 106 is correlated to the active ingredient included therein. In this way, the fragrance further provides an olfactory cue to the user of the continuing efficacy of the air treatment material 106. One or more additional use-up cues may be used, such as, for example, appearing and disappearing inks and the like for the visual guide 132 or secondary substrate 140.

A methodology for selecting a fragrance and an active to be incorporated into the air treatment material 106 is provided. For example, a fragrance may be selected to be efficacious for a first specified time period, and an active ingredient may be selected to be efficacious for a second specified time period. In one embodiment, the first and second time periods may be substantially equivalent. Numerous factors may be considered when selecting the fragrance and the active ingredient including, for example, the climate, the strength of the sense of smell of the user, the size of the room where the emanation system may be used, the size of the substrate 102, the amount of air treatment material 106 applied to the substrate, and the like. It should be appreciated that the fragrance can be "keyed" to the active ingredient, or vice versa, to provide the "use-up" cue function.

In one embodiment, the air treatment material includes about 4% of a fragrance and about 0.4% of the active ingredient (e.g., transfluthrin). Using this formulation, about 3 g of air treatment material 106 may be sprayed onto the substrate 102 to provide both mosquito repellency and a pleasantly fragranced room for a time period of about three days. The air treatment material 106 may be reapplied after the third day to repeat the process.

The air treatment material 106 may solely include an active, or for ease of handling, the active may be carried in a hydrocarbon, an alcohol, or a lipophilic or a hydrophilic solvent, mixtures thereof, or other solvent. Alternatively, or in addition, the substrate 102 and/or secondary substrate 140 may also hold a fragrance, a deodorizer, or other air treatment material to which the active is applied to create the air treatment material 106 on the substrate. In one embodiment, the substrate 102 and/or secondary substrate 140 may include the fragrance which only becomes noticeable once adequately saturated with an applied air treatment material 106 and thus serves as a saturation cue to indicate an adequate amount of air treatment material has been applied. It is envisioned that such an arrangement may teach the user to apply a specific amount (the same amount when first used to trigger the saturation cue) each subsequent time when the substrate 102 is recharged.

As shown in FIGS. 1, 2, and 7, the substrate 102 is designed to be attached to the surface 108 via the attachment mechanism 110. The attachment mechanism 110 may include pins or tacks that extend through the substrate 102 in opposing upper corners thereof. In some embodiments, other attachment mechanisms 110 may include electrostatic forces, a hook and loop fastener, a magnet, adhesives, strings, hooks, or the like. In other embodiments, the substrate 102 may be positioned adjacent the surface 108 (e.g., such as a flat surface) without the use of the attachment mechanism 110. The attachment mechanism 110 preferably allows the substrate 102 to be mounted or hung from a vertical or horizontal surface 108, such as, for example, a wall.

As seen in FIGS. 1 and 7, a dispensing device 104 may be used to apply the air treatment material 106 to the substrate 102. One suitable dispensing device 104 includes a container 180 with a sprayer head 182 mounted thereon. The air treatment material 106 is disposed within the container 180, and the sprayer head 182 acts to seal the air treatment material therein and to provide a dispensing mechanism able to controllably release the air treatment material 106. The sprayer head 182 generally includes a body 184 with a manually actuated trigger 186 and a nozzle 188 with an outlet orifice (not shown). Although a specific dispensing device 104 is shown in FIGS. 1 and 7, other manually or electrically actuated dispensing devices may be used.

In one embodiment, the nozzle 188 of the sprayer head 182 is designed to emit a desirable spray pattern that is correlated to the visible guide 132 on the substrate 102. In some embodiments, the sprayer head 182 may be curved or provided with other structure (not shown) having attributes to facilitate spraying. Further, it is anticipated that a conventional trigger sprayer mechanism may be used or a pre-compression pump type spray mechanism. The nozzle 188 of the sprayer head 182 may further include a swirl chamber (not shown) and/or other mechanism that acts to break up and dispense the air treatment material 106 in a desired pattern.

The sprayer head 182 emits enough air treatment material 106 to contact at least a portion of the substrate 102. In particular, in some embodiments, the sprayer head 182 emits between about 0.1 cc to about 0.5 cc per pump, and in one specific embodiment emits about 0.3 cc per pump. One suitable sprayer head 182 for use in the emanation system 100 is the Mini-Trigger™ Curve Fine Mist Sprayer manufactured by MeadWestvaco Corporation (Richmond, Va.).

By coating the substrate 102 with an appropriate air treatment material 106, air contacting the substrate will acquire a portion of the volatile material (e.g., the active), and release it from the emanation system 100. The air treatment material 106 may be applied to one or more portions of the substrate 102 and/or the secondary substrate 140 (or the first emanation surface 160 and/or the second emanation surface 162 shown in FIG. 6).

In one instance, the user may dispense the air treatment material 106 onto the substrate 102. In this instance, the air treatment material 106 may run, or otherwise flow down the front surface 122 thereof, until it contacts the secondary substrate 140. After contacting the secondary substrate 140, the air treatment material 106 may be absorbed by the secondary substrate for the continuing release of the air treatment material into the atmosphere. In this way, the air treatment material 106 is not wasted due to loss from the air treatment material flowing off the substrate 102 after application thereto.

Application of the air treatment material 106 to the substrate 102 may provide an additional advantage of staged release of the air treatment material. More particularly, a quantity of air treatment material 106 may be released from the substrate 102 in the time period initially following application. Such release provides for faster efficacy of the air treatment material 106. Additionally, runoff from the air treatment material 106 is absorbed into the secondary substrate 140. The runoff quantity of air treatment material 106 is initially absorbed, but continues to be released from the secondary substrate 140 over an extended time period. In some embodiments, the positioning of the secondary substrate 140 allows for runoff to be retained and to be continually released over a longer time period, providing for both initial and continuing efficacy.

Prior to use, the substrate 102 is preferably provided to a user either by itself or via a sealed container or package (not shown). The user may attach the substrate 102 to the surface 108 using the attachment mechanism 110. At this point, the substrate 102 may not include the air treatment material 106 or may include a portion of it, as described herein elsewhere. As depicted in FIG. 7, when the emanation system 100 is to be used, a user grasps the dispensing device 104 and orients the nozzle 188 of the sprayer 162 in substantial alignment with the substrate 102 and/or visual guide 132, if provided. Once properly oriented, the individual applies inward force to the trigger 186 to manually dispense the air treatment material 106 therefrom. The air treatment material 106 contacts the substrate 102 and coats at least a portion thereof. After the air treatment material 106 is applied to the substrate 102, at least a portion of the air treatment material may travel downwardly over the front surface 122 of the substrate until contacting the secondary substrate 140.

In one particular embodiment, the dispensing device 104 is positioned a distance of not greater than about 60 cm away from the substrate 102. Once properly oriented, the individual manually dispenses the air treatment material 106 therefrom by pressing the manually actuated trigger 186. In one specific embodiment, the user applies the air treatment material 106 onto the substrate 102 by pressing the trigger 186 about ten times to impart at least about 5 mg to about 6 mg of active ingredient onto the substrate 102.

In one embodiment, the air treatment material 106 is designed to be applied to the substrate 102 over a predefined time period. In particular, the air treatment material 106 is designed to be applied to the substrate 102 about every three days. In one embodiment, the time period is about one day. In another embodiment, the time period is between about 1 day and about 7 days. In other embodiments, the air treatment material 106 may be applied by the user as desired.

In another embodiment, the substrate 102 is provided to an individual's home for use by another individual. The second individual arrives at the home of the user with the dispensing device 104 and dispenses the air treatment material 106 onto the substrate 102. The second individual then leaves with the dispensing device 104. The user may then have the substrate 102 recharged, as needed, using a subscription service to have their substrates coated with the air treatment material 106 by the second individual. For example, the second individual may re-coat the substrate 102 every three days, weekly, bi-weekly, bi-monthly, monthly, or over other set time periods. In a further instance, the second individual may deliver supplies or other items in conjunction with the application of the air treatment material 106. In a different embodiment, individuals may take their substrates 102 to a central location (e.g., a church, a community center, etc.) to have the substrate coated with the air treatment material 106.

Any of the embodiments described herein may be modified to include any of the structures or methodologies disclosed in connection with different embodiments. Further, the present disclosure is not limited to the substrate, the attachment mechanism, and/or the dispensing device of the type specifically shown. Still further, the support for any component of any of the embodiments disclosed herein may be chosen or modified to work with various types of substrates consistent with the disclosure herein.

INDUSTRIAL APPLICABILITY

Numerous modifications to the present invention will be apparent to those skilled in the art in view of the foregoing description. Accordingly, this description is to be construed as illustrative only and is presented for the purpose of enabling those skilled in the art to make and use the invention and to teach the best mode of carrying out same. The exclusive rights to all modifications which come within the scope of the appended claims are reserved.

We claim:

1. A method of operating an emanation system, comprising the steps of:

attaching a substrate to a surface, the substrate including a first substrate and a secondary substrate attached to the first substrate;

selecting an air treatment material including a fragrance having a first efficacy time period and an active ingredient having a second efficacy time period;

aligning a nozzle of a dispensing device containing the air treatment material with the substrate; and actuating the dispensing device to spray an amount of the air treatment material onto at least a portion of the substrate, wherein the second efficacy time period is longer than the first efficacy time period, and wherein the secondary substrate is positioned to catch run-off from the amount of air treatment material sprayed onto the substrate.

2. The method of claim 1, wherein the air treatment material passively emanates from the first substrate at a first release rate, and passively emanates from the secondary substrate at a second release rate.

3. The method of claim 1 further including the step of filling the dispensing device.

4. The method of claim 1, wherein the nozzle is aligned with a visual guide on the substrate.

5. The method of claim 1, wherein the amount of air treatment material sprayed is about 3 grams.

6. The method of claim 1, wherein the amount of the air treatment material sprayed onto the substrate provides mosquito repellency and a pleasant fragrance to a room for a time period of about three days.

7. The method of claim 2, wherein the second release rate is slower than the first release rate.

8. A method of operating an emanation system, comprising the steps of:

attaching a substrate to a surface, the substrate including a first substrate having a front surface and a secondary substrate that is flush with the front surface;

aligning a nozzle of a dispensing device containing an air treatment material with the substrate; and actuating the dispensing device to spray an amount of the air treatment material onto at least a portion of the substrate, wherein the secondary substrate is positioned to catch run-off from the amount of air treatment material sprayed onto the substrate, and wherein the air treatment material passively emanates from the first substrate at a first release rate, and passively emanates from the secondary substrate at a second release rate different from the first release rate.

9. The method of claim 8, wherein the second release rate is slower than the first release rate.

10. The method of claim 8, wherein a rear surface of the secondary substrate is flush with the front surface of the first substrate.

11. The method of claim 10, wherein a front surface of the secondary substrate is exposed.

12. The method of claim 8, wherein a lower edge of the secondary substrate is aligned with a lower edge of the first substrate.

13. The method of claim 8, wherein a front surface of the secondary substrate is flush with the front surface of the first substrate.

14. The method of claim 13, wherein the front surface of the secondary substrate is exposed.

15. The method of claim 14, wherein an upper edge of the secondary substrate is aligned with a lower edge of the first substrate.

16. The method of claim 8, wherein the second release rate is slower than the first release rate.

17. The method of claim 16, wherein the first release rate is 0.1 mg/hr to 1 mg/hr.

18. The method of claim 17, wherein the second release rate is 0.05 mg/hr to 0.1 mg/hr.

19. The method of claim 18, wherein the air treatment material includes a fragrance having a first efficacy time period and an active ingredient having a second efficacy time period.

20. The method of claim 19, wherein the second efficacy time period is longer than the first efficacy time period.

\* \* \* \* \*